United States Patent
Yang

(10) Patent No.: US 12,090,184 B2
(45) Date of Patent: Sep. 17, 2024

(54) TRADITIONAL CHINESE MEDICINE COMPOSITION FOR TREATING DERMATOPHYTOSIS AND BROMHIDROSIS AND APPLICATION THEREOF

(71) Applicant: JINGCHU UNIVERSITY OF TECHNOLOGY, Hubei (CN)

(72) Inventor: Yang Yang, Hubei (CN)

(73) Assignee: JINGCHU UNIVERSITY OF TECHNOLOGY, Hubei (CN)

( * ) Notice: Subject to any disclaimer, the term of this patent is extended or adjusted under 35 U.S.C. 154(b) by 55 days.

(21) Appl. No.: 17/919,541

(22) PCT Filed: Jun. 20, 2019

(86) PCT No.: PCT/CN2019/092093
§ 371 (c)(1),
(2) Date: Oct. 18, 2022

(87) PCT Pub. No.: WO2020/211189
PCT Pub. Date: Oct. 22, 2020

(65) Prior Publication Data
US 2023/0120111 A1    Apr. 20, 2023

(30) Foreign Application Priority Data

Apr. 16, 2019 (CN) .......................... 201910302053.1

(51) Int. Cl.
| A61K 36/19 | (2006.01) |
| A61K 36/00 | (2006.01) |
| A61K 36/489 | (2006.01) |
| A61P 31/10 | (2006.01) |

(52) U.S. Cl.
CPC ............ *A61K 36/19* (2013.01); *A61K 36/489* (2013.01); *A61P 31/10* (2018.01)

(58) Field of Classification Search
None
See application file for complete search history.

(56) References Cited

FOREIGN PATENT DOCUMENTS

| CN | 100528856 C | * | 8/2009 |
| CN | 106580850 A | * | 4/2017 |
| CN | 107567754 A | * | 1/2018 |
| CN | 109331111 |   | 2/2019 |
| CN | 109820887 |   | 5/2019 |

OTHER PUBLICATIONS

Wu Qiuyun et al., "Research progress of antibacterial activity and mechanism of Chinese herbal medicine", Journal of Traditional Chinese Veterinary Medicine, with English abstract, Feb. 10, 2018, pp. 1-5.
"International Search Report (Form PCT/ISA/210) of PCT/CN2019/092093," mailed on Sep. 9, 2019, with English translation thereof, pp. 1-4.

* cited by examiner

*Primary Examiner* — Aaron J Kosar
*Assistant Examiner* — Randall O Winston
(74) *Attorney, Agent, or Firm* — JCIPRNET

(57) ABSTRACT

A traditional Chinese medicine composition for treating dermatophytosis and bromhidrosis, which is prepared from radix sophorae flavescentis and peristrophe *japonica*, has synergistic interaction and anti-fungal effects, and is not easy to produce drug tolerance. After performing compatibility of extracts of matrine and peristrophe *japonica*, dermatophytosis and bromhidrosis can be treated, and multiple external preparations can be prepared.

8 Claims, No Drawings

TRADITIONAL CHINESE MEDICINE COMPOSITION FOR TREATING DERMATOPHYTOSIS AND BROMHIDROSIS AND APPLICATION THEREOF

CROSS-REFERENCE TO RELATED APPLICATION

This application is a 371 application of International PCT application serial no. PCT/CN2019/092093 filed on Jun. 20, 2019, which claims the priority benefit of China application no. 201910302053.1, filed on Apr. 16, 2019. The entirety of each of the above mentioned patent applications is hereby incorporated by reference herein and made a part of this specification.

TECHNICAL FIELD

The present disclosure relates to a traditional Chinese medicine composition for treating dermatophytosis and bromhidrosis and an application thereof.

DESCRIPTION OF RELATED ART

Tinea pedis (commonly known as dermatophytosis) is caused by a fungal infection in which the skin lesions often occur on one side (that is, one foot) first, and then the opposite side is infected several weeks or months later. Blisters mainly appear on the belly of the toes and on the side of the toes, most commonly between the third and fourth toes, and also appear on the soles of the feet, which are small deep blisters that can gradually merge into bullae. The skin lesions of tinea pedis have a characteristic, that is, the boundary is clear and can gradually expand outward. Due to the development of the disease or scratching, erosion, exudation, or even bacterial infection, pustules, and the like, may appear, which brings great inconvenience to people's daily life.

The existing anti-fungal drugs include azoles (including imidazoles, triazoles) and polyene anti-fungal drugs, which can effectively treat deep and superficial fungal infections, such as ketoconazole, clotrimazole, Conazole in the imidazoles; fluconazole, itraconazole and voriconazole, in the triazoles; and amphotericin B, in polyenes. However, all of the existing anti-fungal drugs can appear resistant strains, and drug resistance, which has become the main reason for the failure of clinical anti-fungal therapies.

Therefore, it is extremely necessary to develop substances from natural medicines that can prevent and treat dermatophytosis on the basis of the prior art.

SUMMARY

The objectives of the present disclosure: The objectives of the present disclosure is to eliminate the deficiencies of the prior art, a traditional Chinese medicine composition with the effect of treating dermatophytosis and bromhidrosis is screened out through a large number of experiments. The composition of the present disclosure can be used for preparing topical preparations for the anti-fungal use, the prevention and treatment of dermatophytosis, and the treatment of bromhidrosis.

Technical solutions are that: in order to achieve the above objectives, the technical solutions adopted in the present disclosure are as the following.

Provided is a traditional Chinese medicine composition for treating dermatophytosis, which includes radix sophorae flavescentis and *persistrophe japonica*.

As a preferred solution, the above traditional Chinese medicine composition for treating the dermatophytosis is prepared from of 1 to 5 parts of the radix sophorae flavescentis and 1 to 5 parts of the *persistrophe japonica*.

As a preferred solution, the above traditional Chinese medicine composition for treating the dermatophytosis is prepared from radix sophorae flavescentis alkaloid and peristrophe *japonica* water extracts or organic solvent extracts. The organic solvent extracts are methanol, ethanol, acetone, ethyl acetate, chloroform, n-butanol, benzene, ether, petroleum ether, and the like. The extraction methods are a decoction method, a reflux extraction method, an ultrasonic extraction method, a percolation method, a continuous reflux extraction method and a dipping method, which can be selected according to actual requirements.

As a preferred solution, the above traditional Chinese medicine composition for treating the dermatophytosis includes matrine, oxymatrine, hydroxymatrine, n-methylcytisine, anagyrine, baptifoline, and dehydromatrine.

As a preferred solution, in the above traditional Chinese medicine composition for treating the dermatophytosis, the radix sophorae flavescentis alkaloid includes the matrine and the oxymatrine.

In the above traditional Chinese medicine composition for treating the dermatophytosis provided in the present disclosure, the peristrophe *japonica* water extracts are prepared by the following preparation method: taking the *persistrophe japonica*, adding water with the amount 5 times to 20 times the *persistrophe japonica*, extracting the solution 1 to 5 times for 0.5 hours to 2 hours each time, by adopting the immersion method, the decocting method, the reflux extraction method or the continuous reflux extraction method, filtering the extracted solutions, combining the extracted solutions, and then concentrating the combined solution to obtain the peristrophe *japonica* water extracts.

In the traditional Chinese medicine composition for treating the dermatophytosis provided in the present disclosure, the radix sophorae flavescentis alkaloid is prepared by the following preparation method: taking matrine, adding an acid water solution (sulfuric acid, hydrochloric acid, and the like, with a volume concentration of 1% to 5%), with the amount 5 to 20 times the matrine, to the matrine, extracting the solution 1 to 2 times for 0.5 to 3 hours each time, combining the acid-water extracted solutions, adding alkali (such as sodium hydroxide, sodium carbonate, etc.) to the combined solution for alkalization, then extracting the alkalized solution with chloroform 1 time to 3 times, combining the chloroform extracted solutions, concentrating the combined solution to dry, adding water to disperse, passing through a cation exchange resin column, washing with water first, and then eluting with ammonia water to obtain an ammonia-water eluted solution, and concentrating the ammonia-water eluted solution to obtain the matrine.

Provided in the present disclosure is an application of the traditional Chinese medicine composition for treating the dermatophytosis in preparation of a topical preparation for preventing and treating the dermatophytosis. As a preferred solution, the topical preparation includes lotion, ointment, tincture, spray, aerosol, gel and the like.

The traditional Chinese medicine composition for treating the dermatophytosis according to the present disclosure has a remarkable anti-fungal effect, and the fungi include *Candida*, *Aspergillus*, and *Trichophyton*. The application of the traditional Chinese medicine composition for treating the dermatophytosis provided by the present disclosure in the preparation of anti-fungal drugs, the fungi are *Candida albicans, Aspergillus fumigatus, Trichophyton rubrum, Trichophyton mentagrophytes* and *Epidermophyton floccosum* bacteria, and the like.

Provided is a traditional Chinese medicine composition for treating bromhidrosis, which includes radix sophorae flavescentis and *persistrophe japonica*.

The above traditional Chinese medicine composition for treating the bromhidrosis is prepared from 1 to 5 parts of the radix sophorae flavescentis and 1 to 5 parts of the peristrophe *japonica*.

The above traditional Chinese medicine composition for treating the bromhidrosis is prepared from radix sophorae flavescentis alkaloid and peristrophe *japonica* water extracts or organic solvent extracts.

In the above traditional Chinese medicine composition for treating the bromhidrosis, the radix sophorae flavescentis alkaloid includes matrine, oxymatrine, hydroxymatrine, n-methylcytisine, Anagyrine, Baptifoline, and Dehydromatrine.

In the above traditional Chinese medicine composition for treating the bromhidrosis, the radix sophorae flavescentis alkaloid includes the matrine and the oxymatrine.

In the above traditional Chinese medicine composition for treating the bromhidrosis, the peristrophe *japonica* water extracts are prepared by the following preparation method: taking the peristrophe *japonica*, adding water with the amount 5 to 20 times the peristrophe *japonica*, extracting the solution 1 time to 3 times for 0.5 hours to 2 hours each time, by adopting the immersion method, the decocting method, the reflux extraction method or the continuous reflux extraction method, filtering the extracted solutions, combining the extracted solutions, and then concentrating the combined solution to obtain the peristrophe *japonica* water extracts.

In the above traditional Chinese medicine composition for treating the bromhidrosis, the radix sophorae flavescentis alkaloid is prepared by the following preparation method: taking matrine, adding an acid water solution, with the amount 5 times to 20 times the matrine, to the matrine, extracting the obtained solution 1 time to 5 times for 0.5 hours to 3 hours each time, combining the acid-water extracted solutions, adding alkali to the combined solution for alkalization, then extracting the alkalized solution with chloroform 1 time to 5 times, combining the chloroform extracted solutions, concentrating the combined solution to dry, adding water to disperse, passing through a cation exchange resin column, washing with water first, and then eluting with ammonia water to obtain an ammonia-water eluted solution, and concentrating the ammonia-water eluted solution to obtain the matrine.

Provided in the present disclosure is an application of the traditional Chinese medicine composition for treating the bromhidrosis in preparation of a topical preparation for preventing and treating the bromhidrosis.

Provided in the present disclosure is the application of the traditional Chinese medicine composition for treating the dermatophytosis in preparation of the topical preparation for preventing and treating the bromhidrosis. The topical preparation is lotion, ointment, tincture, spray, aerosol, gel, and the like. When preparing tinctures, sprays and aerosols, the concentration of ethanol can be adjusted to 30% to 99% according to actual requirements.

The Beneficial effects lie in the following: compared with the prior art, the traditional Chinese medicine composition for treating the dermatophytosis provided by the present disclosure has the following advantages.

1. In the present disclosure, the composition with radix sophorae flavescentis and peristrophe *japonica* as main components is screened out through a large number of experiments, and it is shown through the anti-fungal experimental results that the combination of radix sophorae flavescentis and peristrophe *japonica* can play a synergistic anti-fungal effect, has a better anti-fungal activity than the same dose of single radix sophorae flavescentis or peristrophe *japonica*, is not easy to produce durability, and has a better curative effect, which has made an excellent technical progress.

2. Moreover, it is shown through the experimental results that, after the compatibility of radix sophorae flavescentis alkaloid and peristrophe *japonica* extracts, the composition can play an obvious synergistic effect on the treatment of bromhidrosis with an effective rate of 100%, compared with the same dose of single radix sophorae flavescentis alkaloid and peristrophe *japonica* extracts, the composition has a better anti-bromhidrosis effect that is not easy to recur, and has a definite curative effect.

3. In the present disclosure, the radix sophorae flavescentis and peristrophe *japonica* extracts are prepared into a topical preparation such as lotion, tincture or ointment, which is convenient to use and has a strong practicability.

DESCRIPTION OF THE EMBODIMENTS

The present disclosure can be better understood according to the following examples. However, those skilled in the art would easily understand that the specific material ratios, process conditions and results described in the examples are only used to illustrate the present disclosure, and should not and will not limit the the present disclosure detailed in the claims.

Example 1

1. Provided is a traditional Chinese medicine composition for treating dermatophytosis and bromhidrosis, which includes 1 g of radix sophorae flavescentis alkaloid and 1 g of peristrophe *japonica* extracts.

The above peristrophe *japonica* extracts are prepared by the following preparation method: taking the peristrophe *japonica*, adding water with the amount 10 times the peristrophe *japonica*, extracting the solution 2 times for 1 hour each time by adopting the decocting method, filtering the extracted solutions, combining the extracted solutions, and then concentrating the combined solution to obtain the peristrophe *japonica* extracts.

The above radix sophorae flavescentis alkaloid is prepared by the following preparation method: taking matrine, adding an sulfuric acid solution, having the volume concentration of 5% with the amount 12 times the matrine, to the matrine, reflux-extracting the solution 2 times for 1.5 hours each time, combining the acid-water extracted solutions, adding sodium hydroxide to the combined solution for alkalization to pH in the range of 10 to 11, then extracting the alkalized solution with chloroform 3 times, combining the chloroform extracted solutions, concentrating the combined solution to dry, adding water to disperse, passing through a 732 strong acidic styrene cation type exchange resin column, washing with water until colorless first, and then eluting with ammonia water to obtain an ammonia-water eluted solution, and concentrating the ammonia-water eluted solution to obtain the radix sophorae flavescentis alkaloid. The radix sophorae flavescentis alkaloid, including matrine, oxymatrine, hydroxymatrine, n-methylcytisine, anagyrine, baptifoline, and dehydromatrine, is determined by a high performance liquid chromatography.

Example 2

1. Provided is a traditional Chinese medicine composition for treating dermatophytosis and bromhidrosis, which includes 4 g of radix sophorae flavescentis alkaloids and 1 g of peristrophe *japonica* extracts.

The above peristrophe *japonica* extracts are prepared by the following preparation method: taking the peristrophe *japonica*, adding water with the amount 12 times the peristrophe *japonica*, extracting the solution 3 times for 1 hour each time by adopting the reflux extraction method, filtering the extracted solutions, combining the extracted solutions, and then concentrating the combined solution to obtain the peristrophe *japonica* extracts.

The above radix sophorae flavescentis alkaloids are prepared by the following preparation method: taking matrine, adding an sulfuric acid solution, having the volume concentration of 5% with the amount 10 times of the matrine, to the matrine, reflux-extracting the solution 3 times for 1 hour each time, combining the acid-water extracted solutions, adding sodium hydroxide to the combined solution for alkalization to pH in the range of 10 to 11, then extracting the alkalized solution with chloroform 3 times, combining the chloroform extracted solutions, concentrating the combined solution to dry, adding water to disperse, passing through a 732 strong acidic styrene cation type exchange resin column, washing with water until colorless first, and then eluting with ammonia water to obtain an ammonia-water eluted solution, and concentrating the ammonia-water eluted solution to obtain the radix sophorae flavescentis alkaloids. The radix sophorae flavescentis alkaloids, including the matrine, oxymatrine, hydroxymatrine, n-methylcytisine, anagyrine, baptifoline, and dehydromatrine, are determined by a high performance liquid chromatography.

Example 3

1. Provided is a traditional Chinese medicine composition for treating dermatophytosis and bromhidrosis, which includes 1 g of radix sophorae flavescentis alkaloid and 4 g of peristrophe *japonica* extracts.

The above peristrophe *japonica* extracts are prepared by the following preparation method: taking the peristrophe *japonica*, adding water with the amount 8 times the peristrophe *japonica*, extracting the solution 2 times for 1.5 hours each time by adopting the reflux extraction method, filtering the extracted solutions, combining the extracted solutions, and then concentrating the combined solution to obtain the peristrophe *japonica* extracts.

The above radix sophorae flavescentis alkaloid is prepared by the following preparation method: taking matrine, adding an sulfuric acid solution, having the volume concentration of 5% with the amount 8 times the matrine, to the matrine, reflux-extracting the solution 3 times for 1 hour each time, combining the acid-water extracted solutions, adding sodium hydroxide to the combined solution for alkalization to pH in the range of 10 to 11, then extracting the alkalized solution with chloroform 3 times, combining the chloroform extracted solutions, concentrating the combined solution to dry, adding water to disperse, passing through a 732 strong acidic styrene type cation exchange resin column, washing with water until colorless first, and then eluting with ammonia water to obtain an ammonia-water eluted solution, and concentrating the ammonia-water eluted solution to obtain the radix sophorae flavescentis alkaloid. The radix sophorae flavescentis alkaloid, including matrine, oxymatrine, hydroxymatrine, n-methylcytisine, anagyrine, baptifoline, and dehydromatrine, is determined by a high performance liquid chromatography.

Example 4 Anti-Fungal Activity Experiment

1. The present disclosure conducts an in vitro anti-fungal test on the composition extracts in Examples 1 to 3, and the single radix sophorae flavescentis alkaloid and single peristrophe *japonica* extracts prepared in Example 3. The cell strains used in the test are all ATCC standard strains provided by the Fungi Center of the Medical Microbial (Virus) Species Collection and Management Center of the Ministry of Health, which includes as follows, *Aspergillus: Aspergillus fumigatus* Strain Number: CMCCC(F) A1g (ATCC-MYA-3626); *Candida: Candida albicans* Strain Number: CMCCC (F) C.1L (ATCC90028); *Trichophyton: Trichophyton rubrum* Strain Number: CMCCC(F)T.1h (ATCC-MYA-4438); *Trichophyton mentagrophytes* Strain Number: CMCCC(F)T.5e (ATCC-MYA-4439).

2. The specific experimental methods are carried out with reference to the standard methods of yeast M-27A3 and filamentous fungi M-38P issued by the Clinical and Laboratory Standards Institute (US, CLSI) of the United States.

3. Experimental Methods

The preparation of the bacterium solution is as follows.

Before the experiment, after activating the experimental bacteria, yeast are cultured on Sabouraud Dextrose Agar (SDA) medium at 30° C. for 48 hours; filamentous fungi are cultured on potato dextrose agar (PDA) medium at 26° C. for 7 days to 10 days. A suspension is prepared with sterile normal saline, the suspension is counted by a hemocytometer, and is dilute with RMPI-1640 liquid medium containing 2% glucose in multiple amounts to *Candida albicans* $1.0 \times 10^3$ cfu/mL; the other three filamentous fungi are prepared into $2.5 \times 10^4$ cfu/mL. 0.1 mL of bacterial solutions are taken respectively, the culture medium containing the compositions prepared in Examples 1 to 3 and the same doses of the radix sophorae flavescentis alkaloids and the peristrophe *japonica* extracts prepared in Example 3 are added into each well, wherein the well 11 is a vehicle control, the well 12 is a medium control. 0.1 mL of the diluted solvent is added into the vehicle control well, and 0.1 mL of the distilled water is added into the control well. After adding the sample, it is put on the shaker with the rotation speed of 100 r/min×10 min, so that the drug and the bacterial solution are in a full contact. A 2% glucose-containing RMPI-1640 liquid medium without any antibiotics is taken as the basal medium. The positive control drug is itraconazole.

4. A Method for Determining the Experimental Results

80% Minimum Inhibitory Concentration (80% MIC): with reference to the growth of the bacteria in the blank control well and the vehicle control well, when the bacteria in the drug base well only grows 80%, it is indicated that there is a bacteriostatic effect, and when the bacteria have grown, it is indicated that there is no bacteriostatic effect. The experimental results are as shown in Table 1 below.

TABLE 1

| Determination results of 80% MIC of the composition on fungi | | | | |
| --- | --- | --- | --- | --- |
| | *Aspergillus fumigatus* ATCC-MYA-3626 | *Candida albicans* ATCC90028 | *Trichophyton rubrum* ATCC-MYA-4438 | *Trichophyton mentagrophytes* ATCC-MYA-4439 |
| Compositions prepared in Example 1 | 8.6 | 7.2 | 7.1 | 6.9 |
| Compositions prepared in Example 2 | 7.3 | 6.8 | 6.9 | 6.2 |
| Compositions prepared in Example 3 | 4.7 | 5.3 | 6.1 | 5.4 |
| Radix Sophorae Flavescentis Alkaloid | 12.2 | 13.8 | 16.8 | 8.2 |
| *Peristrophe Japonica* Extracts | 10.8 | 8.9 | 8.5 | 7.8 |
| Itraconazole | 4.2 | 3.8 | 5.6 | 5.8 |

It is shown from the experimental results in Table 1 above that, the composition provided by the present disclosure has an excellent bacteriostatic effect on a variety of fungi, the composition can play an obvious synergistic interaction effect especially after the compatibility of radix sophorae flavescentis and the peristrophe *japonica* extracts, and the composition has a better antibacterial effect in comparison with the same dose of radix sophorae flavescentis and peristrophe *japonica* extracts, in particular, the antibacterial effect is more effective when the weight ratio of radix sophorae flavescentis alkaloid and the peristrophe *japonica* extracts is 1:4.

Example 5 Examples of the Effect on Treating the Dermatophytosis

Thirty patients with dermatophytosis are selected, including 20 males and 10 females, aged from 12 to 60 years old, with an average age of 38 years old. 20 g of the composition prepared in Example 3 of the present disclosure is used every day, and the feet are soaked in hot water with the dissolved composition for 30 minutes; after soaking the feet for 7 days, the patient's odor and itching disappear, and the inflammation at the skin rupture disappears with the total effective rate of 100%; after soaking the feet for 14 days, the cure rate is 86%, and there is no recurrence during a follow-up two months later.

Example 6 Examples of the Effect on Treating the Bromhidrosis

1. In the present disclosure, the composition extracts of Examples 1 to 3, and the single radix sophorae flavescentis alkaloid and peristrophe *japonica* extracts prepared in Example 3 are dissolved with 75% ethanol, and an in vitro anti-fungal test is carried out.

2. Case selection: sixty patients with bromhidrosis from June 2018 to Jun. 2019, 30 males and 30 females, are selected and divided into 6 groups with 10 cases in each group.

3. Treatment method: in Groups 1 to 3, the same dose of the 75% ethanol solution (the weight volume ratio of the extracts and 75% ethanol is 1:5) of the composition extracts in Examples 1 to 3 of the present disclosure is adopted for scrubbing; in Groups 4 to 5, the same dose as Groups 1 to 3 of the 75% ethanol solution (the weight volume ratio of the extracts and 75% ethanol is 1:5) of a single radix sophorae flavescentis alkaloid and a single peristrophe *japonica* extract prepared in Example 3 is adopted for scrubbing; in Group 6, the 75% ethanol solution is adopted for scrubbing; in the above six groups, all of the patients are scrubbed once every morning and every evening with a dosage of 4 mL and with a treatment course of one month.

4. Determination criteria: after one treatment course, the bromhidrosis of underarm body odor is completely eliminated, and no recurrence within two months is markedly effective; after one treatment course, underarm body bromhidrosis is relieved, there is smell in the vicinity, and there is no bromhidrosis in the distance, and no recurrence within two months is effective; after one treatment course, the symptoms are not significantly improved as invalid.

5. The specific experimental results are as shown in Table 2 below.

TABLE 2

| Experimental results of treatment of body odor in each group: | | | | | | |
| --- | --- | --- | --- | --- | --- | --- |
| Group | number of cases | marked effective | effective | ineffective | marked effective rate (%) | effectiverate (%) |
| Example 1 | 10 | 6 | 4 | 0 | 60 | 100 |
| Example 2 | 10 | 7 | 3 | 0 | 70 | 100 |
| Example 3 | 10 | 8 | 2 | 0 | 80 | 100 |
| Radix Sophorae *Flavescentis* Alkaloid | 10 | 4 | 5 | 1 | 40 | 90 |
| *Peristrophe Japonica* Extracts | 10 | 3 | 4 | 3 | 30 | 70 |
| 75% Ethanol | 10 | 0 | 0 | 10 | 0 | 0 |

It can be known from Table 2 that, after the compatibility of radix sophorae flavescentis alkaloid and peristrophe *japonica* extracts, the composition can play an obvious synergistic interaction effect on treating bromhidrosis with the effective rate of 100%, especially the composition in Example 3 has a marked effective rate of 80%, which has a better anti-body bromhidrosis effect in comparison with the same dose of radix sophorae flavescentis alkaloid and peristrophe *japonica* extracts.

Example 7 Bromhidrosis Cases

Zhou who is a female white-collar worker in a professional company and aged 33 years old, adopts the ethanol solution of the radix sophorae flavescentis alkaloid and the peristrophe *japonica* extracts in Example 3 of the present disclosure for spraying twice every day. After a continuous treatment for two weeks, the bromhidrosis is obviously weakened and the bromhidrosis can not be smelled in the vicinity (within one meter); after a continuous treatment for one month, the bromhidrosis is significantly improved and no bromhidrosis appears after an exercise; after a continuous treatment for two months, the bromhidrosis under her armpits is completely eliminated, and no recurrence appears during a follow-up one year later.

Zhang who is a male driver aged 45 years old with a moderate bromhidrosis that aggravates after exercise, adopts the ethanol solution of the radix sophorae flavescentis alkaloid and the peristrophe *japonica* extracts in Example 3 of the present disclosure for spraying twice every day. After a continuous treatment for two weeks, the bromhidrosis is significantly weakened and the bromhidrosis can not be smelled in the vicinity (within two meters); after a continuous treatment for one month, the bromhidrosis is significantly weakened and the bromhidrosis can not be smelled in the vicinity (within one meter); after a continuous treatment for two months, the bromhidrosis does not appear after an exercise; and after a continuous treatment for three months, the bromhidrosis under his armpits is completely eliminated, and no recurrence appears during a follow-up one year later.

Liu is a male student at school aged 19 years old, he starts to get the bromhidrosis in adolescence, and it is extremely easy for him to smell a particularly pungent odor under his armpits in summer or when he is sweaty. He adopts the ethanol solution of the radix sophorae flavescentis alkaloid and the peristrophe *japonica* extracts in Example 3 of the present disclosure for spraying twice every day. After a continuous treatment for four weeks, the bromhidrosis is significantly reduced, and the bromhidrosis can not be smelled in the vicinity (within two meters); after a continuous treatment for one month, the bromhidrosis is significantly reduced, and the bromhidrosis can not be smelled in the vicinity (within two meters); after a continuous treatment for two months, the bromhidrosis does not appear after an exercise; after a continuous treatment for three months, the bromhidrosis under his the armpit is completely eliminated, and no recurrence appears during a follow-up one year later.

The above implementations are only intended to illustrate the technical concepts and characteristics of the present disclosure, and their objectives are to allow those who are familiar with the technology to understand the contents of the present disclosure and implement them, and cannot limit the protection scope of the present disclosure. All equivalent changes or modifications made according to the spirits of the present disclosure should be covered within the protection scope of the present disclosure.

What is claimed is:

1. A topical traditional Chinese medicine in an effective amount for treating dermatophytosis, wherein the traditional Chinese medicine comprises Radix sophorae flavescentis and *Persistrophe japonica*, wherein the traditional Chinese medicine is prepared from 1 to 5 parts of the Radix sophorae flavescentis and 1 to 5 parts of *Persistrophe japonica*, and wherein the traditional Chinese medicine is prepared from (i) Radix sophorae flavescentis alkaloid and (ii) *Persistrophe japonica* water extracts or organic solvent extracts of the *Persistrophe japonica*.

2. The topical traditional Chinese medicine in an effective amount for treating the dermatophytosis according to claim 1, wherein the Radix sophorae flavescentis alkaloid comprises matrine, oxymatrine, hydroxymatrine, N-methylcytisine, anagyrine, baptifoline, and/or dehydromatrine.

3. The topical traditional Chinese medicine in an effective amount for treating the dermatophytosis according to claim 2, wherein the Radix sophorae flavescentis alkaloid comprises matrine and oxymatrine.

4. The topical traditional Chinese medicine according to claim 1, wherein the topical medicine is in the form of a lotion, ointment, tincture, spray, aerosol, or gel.

5. A method comprising administering to a subject for treating dermatophytosis the topical traditional Chinese medicine of claim 1.

6. A topical traditional Chinese medicine in an effective amount for treating bromhidrosis, wherein the traditional Chinese medicine comprises Radix sophorae flavescentis and *Persistrophe japonica*, wherein the traditional Chinese medicine is prepared from 1 to 5 parts of the Radix sophorae flavescentis and 1 to 5 parts of *Persistrophe japonica*, wherein the traditional Chinese medicine is prepared from (i) Radix sophorae flavescentis alkaloid and (ii) *Persistrophe japonica* water extracts or organic solvent extracts of the *Persistrophe japonica*.

7. The topical traditional Chinese medicine according to claim 6, wherein the topical medicine is in the form of a lotion, ointment, tincture, spray, aerosol, or gel.

8. A method comprising administering to a subject for treating bromhidrosis the topical traditional Chinese medicine of claim 6.

* * * * *